Figure 1:
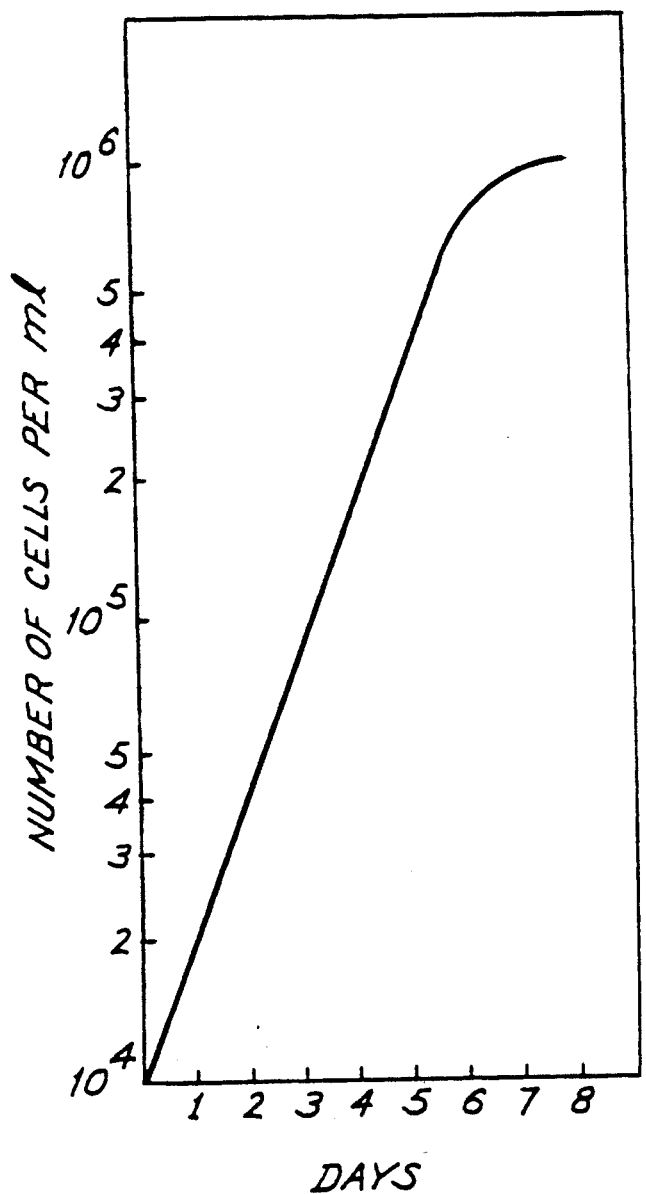

United States Patent [19]

Bertheussen

[11] Patent Number: 5,045,467
[45] Date of Patent: * Sep. 3, 1991

[54] SERUM-FREE GROWTH MEDIUM AND USE THEREOF

[75] Inventor: Kjell Bertheussen, Eidkjosen, Norway

[73] Assignees: Medi-Cult A/S, Oslo, Norway; A/S GEA Farmaceutisk Fabrik, Fredriksberg, Denmark

[*] Notice: The portion of the term of this patent subsequent to Sep. 3, 2008 has been disclaimed.

[21] Appl. No.: 142,069

[22] Filed: Jan. 11, 1988

[30] Foreign Application Priority Data

Jan. 9, 1987 [NO] Norway .................................. 870095

[51] Int. Cl.$^5$ .............................................. C12N 5/02
[52] U.S. Cl. ............................. 435/240.31; 435/240.3
[58] Field of Search ............. 435/240.3, 240.6, 240.31; 935/110

[56] References Cited

U.S. PATENT DOCUMENTS

| | | | |
|---|---|---|---|
| 4,466,917 | 8/1984 | Nussenzweig et al. | 935/6 |
| 4,520,020 | 5/1985 | Loebenstein | 435/70.1 |
| 4,544,632 | 10/1985 | Yamamura et al. | 435/240.26 |
| 4,568,544 | 2/1986 | Hasegawa et al. | 435/240.24 |
| 4,604,284 | 8/1986 | Kung et al. | 435/69.51 |

FOREIGN PATENT DOCUMENTS

| | | |
|---|---|---|
| 0174155 | 3/1986 | European Pat. Off. . |
| EP0174155 | 3/1986 | European Pat. Off. . |
| 3007780 | 1/1988 | Japan . |

OTHER PUBLICATIONS

The Merck Index, Merck & Co., Rahway, N.J., 1983, pp. 330–331.
Ham et al., "Media and Growth Requirements", pp. 51–52 in Jakoky et al., Methods in Enzymology, vol. LVIII, 1979, Academic Press, N.Y.
Bertheussen, et al., (1989), Human Reprod., 4(5):531–535.
Kirk-Othmer, Encyclopedia of Chemical Technology, vol. 19:511–564.
Nielsen et al., (1989), Cytotechnology, Supp. 79.
Iscove et al., J. Exp. Med., 147:923–933 (1978).
Ham, R. G., In: Growth of Cells in Hormonally Defined Media, Cold Spring Harbor Conference on Cell Proliferation; 9; pp. 39–60 (1982).
Barnes et al., Anal. Biochem., 102:255–270 (1980).
Stein, J. R., Handbook of Physiological Methods, Chapt. 1, 7–51 (1973).
Kruse, P. et al., Tissue Culture Methods and Applications, Section XIV, 671–697 (1973).

Primary Examiner—Jacqueline Stone
Assistant Examiner—George C. Elliott
Attorney, Agent, or Firm—Arnold, White & Durkee

[57] ABSTRACT

Serum-free growth medium comprising an iron-chelate, aurin-tricarboxylic acid and optionally alkali-metal-EDTA and trace elements together with possible growth factors, wherein the iron-chelate may comprise a mixture of Fe-EDTA and citric acid. The growth medium may be used for quality testing of other growth media, optionally together with a hybridoma cell line from $p_3U_1$ tumor cells and B-lymphocytes, which hybridoma also is disclosed.

26 Claims, 1 Drawing Sheet

SERUM-FREE GROWTH MEDIUM AND USE THEREOF

BACKGROUND OF THE INVENTION

It has long been a problem with cultivating cells that they require iron as a necessary component in the medium. To present the iron molecules to the cell membrane, it has previously been necessary to add transferrin, usually through addition of serum, to the growth medium. However, such an addition of serum will also produce several disadvantages.

It has been found that aurintricarboxylic acid will present iron to the cell membrane equally well, thus avoiding the addition of serum to the growth medium.

However, to bring the iron into a form which may avoid that the element precipitating from the solution, it is necessary to add chelating agents to the medium. This, taken together with the action of aurintricarboxylic acid, makes it preferable to add EDTA and citric acid/citrate to the medium (or the additive according to the invention, whichever the case may be). Thus, the citric acid is not added to adjust the pH, but is added as a chelator (though it may incidentally also have pH-adjusting properties as well). However, EDTA is just an example of a chelating agent to make a stable iron chelate, and any biocompatible chelating agent (and several are known in the art of cultivating cells) may be used. As mentioned above, the main consideration is that aurintricarboxylic acid presents the iron in solution to the cell membrane.

The present invention concerns a serum-free medium which may be used in culturing cells which require iron in the growth medium. The invention may be used to test the quality of other growth media in addition to that it is possible to culture cells in media which are free from serum.

There has in industry and research long been a large need of serum-free media and growth cultures since the supply of serum to such media gives the solutions, in addition to the compounds which are necessary for growth, also compounds that influence most expriments negatively where accracy of the results are of great importance. This is valid within discipline such as cellular immunology, biotechnology, "in vitro" fertilization, organ transplants, cancer research and by storing and transfusion of blood.

Those media and physiological solutions which today are used in research, industry and by clinical work, are today based on up to 100 year old recipies, and represent thus a "stand-still" in this field of biological research. Media used until today for cell cultures comprise most often a so-called "commercial base medium" to which there is added approximately 10% heat inactivated serum. This very old method comprises the following disadvantages:

1) The heat treatment which is necessary to prevent the lytic effect of the serum on cells, has a denaturing effect on important serum components.

2) Different serum batches have different properties on account of their origin, something which adds unwanted variations to the behaviour of the cell cultures "in vitro".

3) Serum contains several unknown factors and compounds with unknown and uncontrolled effect on cells.

4) Serum is an unphysiological fluid for most cells since the cells are adapted to the so-called tissue-fluid in the body, whereby this fluid has a different content of different compounds compared to serum.

5) Antibodies in serum may bind to cells and interfere with experiments.

6) Serum prevents the study of the cell's synthesis of serum factors "in vitro" since the "background level" in serum of such factors is relatively high.

By using the serum-free medium according to the present invention, the above mentioned disadvantages are avoided, and such a medium will in addition be very properly suited for culturing and storing cells and tissue "in vitro". In addition the complete medium according to the invention will be specifically defined, be serum free, protein free (except for possibly a small quantity of insulin which is required by some cells, and which is used where necessary), contain iron and trace elements as stabilized, chelated elements or compounds without transferrin or lipid being present. The medium according to the invention is also very cheap to produce.

The main problem of previous serum-free media (see N. N. Iscove and F. Melchers, "Complete Replacement of Serum by Albumin, Transferrin, and Soybean Lipid in Cultures of Lipopolysaccharide-reactive B-lymphocytes", J. Exp. Med., Vol. 147, pp. 923–933 (1978); R. G. Ham, "Importance of the Basal Nutrient Medium in the Design of Hormonally Defined Media", in: Growth of Cells in Hormonally Defined Media, Cold Spring Harbor Conference on Cell Proliferation, Vol. 9, pp. 39–60 (1982); D. Barnes and G. Sato, "Methods for Growth of Cultured Cells in Serum-free Medium", Anal. Biochem. 102, pp. 255–270 (1980)) is that they are not suitable for application to a randomly chosen cell culture on account of two circumstances:

1) The presence of physiological amounts of bicarbonate and $Ca^{2+}/Mg^{2+}$-ions will precipitate iron and trivalent trace metals from almost any known chelator system at 37° C. and pH 7–8 (except transferrin). This conclusion arises from the Applicant's personal work (not made public).

2) The concentration of trace metals including toxic compounds in a medium is not controlled, and will vary significantly depending on the composition and the individual properties of the water and impurities therein. The only solution to this problem is to produce a completely stable metal ion buffer comprising a balanced solution of all the necessary trace elements and metals, and thus the toxic metals will be absorbed by the buffer (the toxic effect will become balanced away).

Since transferrin is expensive and species-specific, the medium according to the invention was produced, based on a Fe/trace-element buffer of synthetic non-protein chelators, and where the main problem, precipitation of metals at 37° C. (see above), was solved by adding certain chelators which, when mixed together in solution, have very different and unique properties compared to each chelator alone. The chelators chosen were EDTA and citrate, where the ratio of citrate buffer to EDTA was about 3:1 or greater by molar concentrations. In this respect it is understood that a citrate buffer represents the sum of citrate and citric acid.

The second problem, namely presentation of iron to the cell membrane and the cell, was solved by addition of aurin-tricarboxylic acid to the medium. Even if EDTA/citrate makes the metal solution completely stable, different animal or human cells will not grow because of iron deficiency. It is found that the combination EDTA/citrate/aurin-tricarboxylic acid produces outstanding chelating and iron presenting properties which previously have not been described. (In this connection it is of no consequence that EDTA along previously has been used as an iron chelator for growth of plant cells at pH 5.0 under conditions where metal precipitation does not represent any problem; see: P. Kruse and M. K. Petterson, "Tissue Culture Methods and Applications", Acad. Press (1973); J. R. Stein, "Handbook of Physiological Methods", Cambridge University Press (1973).)

In connection with cell growth it is found that a ratio between EDTA and citric acid (citrate) of respectively 1:10 as an example, was very advantageous. It shall also be mentioned briefly that cell growth in media usually is performed at pH 7.4, but that pH in the final medium according to the present invention also may be between about 7.0–7.8, depending on the growth requirements of the various cells. Accordingly, a serum-free growth medium comprising a 2.4–3.6 micromolar concentration of aurintricarboxylic acid may be provided.

Growth medium according to the present invention may be produced as an example by adding a concentrated solution of each component to pure water (it is of great importance to use water of highest possible purity, such as for instance "Travenol" sterile water, when making the medium according to the invention. An example of such a concentrated mixture produced below is a 1000-fold media additive composition which may be used to culture cells in a 1000-fold diluted form of the media additive.

| | | Weight per 100 ml water |
|---|---|---|
| 3 mM | Fe-EDTA[1] | 120.1 mg |
| 3 mM | Aurin-tricarboxylic acid[2] | 126.7 mg |
| 1 mM | Na$_2$-EDTA | 37.2 mg |
| 15 mM | Citric acid | 315.0 mg |
| 25 mM | Na$_3$-citrat | 735.0 mg |
| (optionally 1% v/v trace elements[3]) | | |

[1] Ethylenediaminetetraacetic acid Fe(III)-Na chelate dihydrate. (Koch-Light No. 2529-00)
[2] Sigma A 1895
[3] May be as the trace element composition given below.

The pH of the composition is preferably adjusted to a pH in the range of about 4.5–5.0.

Optional addition of trace elements may as an example be performed by help of a stem solution which may be produced as given below. The given solution will have a 100 000 fold concentration of the one that is used in the medium. By producing the solution given below, Zn, Cu and chelators (EDTA and citrate) ought to be added prior to adjusting the pH to 5.0 with 5–10N NaOH, whereafter the additional components are added. The final pH ought to lie between 4.0 and 4.5.

| Trace metal (conc.) | Salt | Weight per 100 ml water |
|---|---|---|
| 10 mM Zn | ZnSO$_4$.7H$_2$O | 287.5 mg |
| 2 mM Cu | CuSO$_4$.5H$_2$O | 49.9 mg |
| 0.1 mM Mn | MnSO$_4$.H$_2$O | 1.7 mg |
| 0.02 mM Ni | Ni(NO$_3$)$_2$.6H$_2$O | 0.58 mg |
| 0.2 mM Al | NH$_4$Al(SO$_4$)$_2$.12H$_2$O | 9.2 mg |
| 0.1 mM Cr | KCr(SO$_4$)$_2$.12H$_2$O | 5.0 mg |
| 0.02 mM Co | CoCl$_2$.6H$_2$O | 0.48 mg |
| 1 mM Se | SeO$_2$ | 11.1 mg |
| 14 mM Na$_2$-EDTA | | 521.1 mg |
| 1 mM Na$_3$-citrat | | 29.4 mg |

It is of course to be understood that such a composition of trace elements may contain other elements than those which are given in the table above, depending on the requirements of the used tissue or cell types.

The medium according to the invention may, in addition to the components which are given previously, also contain growth stimulating and necessary compounds for cell growth. Such compounds may comprise for instance the surfactant Pluronic F 68 (20 mg/l), D-glucose (2.5 g/l), L-glutamine (2 mM), Na-pyruvate (1 mM), Insulin (0.5 mg/l) or ethanolamine (20 uM). All the in paranthesis given concentrations refer to final concentrations. An additional composition of the mentioned compounds (with exception of ethanolamine which is a fluid at room temperature) may be produced as a dry product, and as such this may be stored during extended periods of time, up to several years. Ethanolamine may if required be added to the medium in the wanted concentration when using the composition. Ethanolamine is most often used in experiments with hybridomas by production of monoclonal antibodies.

A preferred basal medium wherein the medium addition according to the present invention may be added, is RPMI 1640 w/2.5 g/l NaHCO$_3$ and 20 mM HEPES (N-2-hydroxyethylpiperazine-N-N'-2-ethanesulphonic acid).

Preferred cell cultures where the serum-free medium according to the present invention has proven to be especially useful, is with L 929 mouse fibroblast cell-line, HELA human tumor cell line, various mouse- and human B hydridoma cells, which all produce monoclonal antibodies in quantities which correspond to growth serum-containing cultures and human monocytes which differentiate to developed macrophages during 7 days while keeping their complement receptors.

An especially preferred use of the present invention is performed with fast-growing cell types for testing the quality of other types of media. By mixing the serum-free mediumcomposition according to the invention with RPMI 1640 and adding the medium which is to be tested in the ratio serum-free medium additive+RPMI 1640: unknown medium=1:1, and thereafter adding a number of approximately 30.000 cells/ml, there will, without any toxic compounds present in the medium that is to be tested, be observed an increase in the cell number after 4 days of approximately 10 times more cells than the original number. If, however, toxic compounds are present in the unknown medium, there will not be observed cell growth. This comprises thus a very simple quality test which is extremely sensitive because it is performed without serum, and false results are avoided because one avoids that serum binds and masks toxic impurities.

The growth medium according to the present invention together with the mentioned fast-growing hybridoma cell type may thus be incorporated in a test-kit comprising for instance the serum replacement according to the invention, frozen or growing cells and optionally medium (RPMI 1640) and culture equipment of plastic or other suited material.

As a preferred new cell line that is to be used when for instance testing other growth media as disclosed above, there has been deposited a cell culture at the European Collection of Animal Cell Cultures, Porton Down, Salisbury, Wiltshire SP4 0JG an Nov. 20, 1986 with accession number 86112001. This cell type is a special type of fast-growing hybridoma-type cells made from fusion of P$_3$U$_1$ tumor cells with mouse B-lymphocytes. This cell line has proven to be especially useful at quality testing of other growth media as disclosed previously, and comprises a part of the present invention.

I claim:

1. A serum-free growth medium comprising:
   a) a non-toxic iron chelate; and
   b) aurintricarboxylic acid in a base culture medium, and which has a pH of between about 7.0–7.8.

2. The serum-free growth medium of claim 1 wherein the iron chelate comprises Fe-EDTA and citrate buffer, in a molar ratio of about 1:3.

3. The serum-free growth medium of claim 1 or 2 defined further as including trace elements.

4. The serum-free growth medium of claim 3 further comprising a surfactant.

5. The serum-free growth medium of claim 3 further comprising the surfactant Pluronic F 68.

6. The serum-free growth medium of claim 3 further comprising serum-free growth factors.

7. The serum-free growth medium of claim 3, wherein the base medium comprises an RPMI media including 20 mM HEPES and 2.5 g/L $NaHCO_3$.

8. The serum-free growth medium of claim 1 or 2 defined further as comprising a surfactant.

9. The serum-free growth medium of claim 8 wherein the surfactant is Pluronic F 68.

10. The serum-free growth medium of claim 8, wherein the base medium comprises an RPMI 1640 media including 20 mM HEPES and 2.5 g/L $NaHCO_3$.

11. The serum-free growth medium of claim 1 or 2 further comprising serum-free growth factors.

12. The serum-free growth medium of claim 11 wherein the base medium comprises an RPMI 1640 media including 20 mM HEPES and 2.5 g/L $NaHCO_3$.

13. The serum-free growth medium of claim 1 further defined as comprising an alkalimetal-EDTA and trace elements.

14. The serum-free growth medium of claim 1, 2, or 13 further including trace elements selected from the group consisting of Zn, Cu, Mn, Ni, Al, Cr, Co, Se and $Na_2$-EDTA.

15. The serum-free growth medium of claim 14 further comprising:
   100.0 nanomolar Zn;
   20.0 nanomolar Cu;
   1.0 nanomolar Mn;
   0.2 nanomolar Ni;
   2.0 nanomolar Al;
   1.0 nanomolar Cr;
   0.2 nanomolar Co;
   10.0 nanomolar Se; and
   14.0 nanomolar $Na_2$-EDTA.

16. The serum-free growth medium of claim 13 further comprising serum-free growth factors.

17. The serum-free growth medium of claim 1 or 2, wherein the base medium comprises an RPMI 1640 media including 20 mM HEPES and 2.5 g/L $NaHCO_3$.

18. A serum-free growth medium additive comprising Fe-EDTA, aurintricarboxylic acid, and and $Na_3$-citrate with a pH in the range of about 4.5–5.0.

19. The serum-free growth medium additive of claim 18 further comprising 2.4–3.6 mM Fe-EDTA, 2.4–3.6 mM aurintricarboxylic acid, 0.8–1.2 mM $Na_2$-EDTA, 12–18 mM citric acid and 20–30 mM $Na_3$-citrate.

20. The serum-free growth medium additive of claim 18, in the form of a dry-matter composition.

21. The serum-free medium additive of claim 18, wherein the concentration of aurintricarboxylic acid is in the range of 2.4–3.6 mM.

22. The serum-free growth medium additive of claim 18 wherein the concentration of aurintricarboxylic acid is 3 mM.

23. The serum-free growth medium additive of claim 18 further comprising factors selected from the group consisting of D-glucose, L-glutamine, Na-pyruvate, insulin and ethanolamine.

24. The serum-free growth medium additive of claim 18 defined further as comprising ions selected from the group consisting of:
   0.1 mM $Zn^{2+}$
   0.02 mM $Cu^{2+}$
   0.002 mM $Al^{3+}$
   0.001 mM $Cr^{3+}$;
   0.0002 mM $CO^{2+}$; and
   0.01 mM $Se^{4+}$.

25. A serum-free growth medium comprising:
   a) a non-toxic iron chelate;
   b) 3 micromolar Fe-EDTA;
   c) 2.4–3.6 micromolar aurintricarboxylic acid; and
   d) a citrate buffer comprising a mixture of citric acid and citrate,
   wherein the molar ratio of citrate buffer to Fe-EDTA is 10:1.

26. The serum-free growth medium of claim 25 wherein the concentration of aurintricarboxylic acid is 3 micromolar.

* * * * *

UNITED STATES PATENT AND TRADEMARK OFFICE
CERTIFICATE OF CORRECTION

PATENT NO. : 5,045,467
DATED : September 3, 1991
INVENTOR(S) : Kjell Bertheussen It is certified that error appears in the above-indentified patent and that said Letters Patent is hereby corrected as shown below:

In claim 5, column 5, line 17, delete the word "the" and insert therefor --a--.

In claim 18, column 6, line 12, delete the word "about".

In claim 25, column 6, line 39, delete the word "chelate" and insert therefor --chelator--.

Signed and Sealed this

Nineteenth Day of October, 1993

Attest:

BRUCE LEHMAN

*Attesting Officer*    *Commissioner of Patents and Trademarks*